(12) United States Patent
Munagavalasa et al.

(10) Patent No.: US 6,790,670 B2
(45) Date of Patent: Sep. 14, 2004

(54) END OF USE AND TIME DURATION INDICATOR SYSTEM AND METHOD BASED ON VOLATILE DYE

(75) Inventors: Murthy S. Munagavalasa, Kenosha, WI (US); Stacey L. Forkner, Waterford, WI (US); Stanley J. Flashinski, Racine, WI (US); Adam Hagop Buchaklian, East Troy, WI (US); David J. Houser, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 295 days.

(21) Appl. No.: 09/973,504

(22) Filed: Oct. 9, 2001

(65) Prior Publication Data

US 2003/0152483 A1 Aug. 14, 2003

(51) Int. Cl.$^7$ ................................................ G01N 21/78
(52) U.S. Cl. ........................ 436/164; 436/166; 422/58; 422/61; 424/409; 424/411
(58) Field of Search .............................. 422/56, 58, 61; 436/104, 164, 166, 169; 424/409, 411

(56) References Cited

U.S. PATENT DOCUMENTS

| 805,560 A | 11/1905 | Kohn | |
| 2,431,924 A | 12/1947 | Dunaway | 299/24 |
| 3,409,404 A | 11/1968 | Fergason | 23/230 |
| 3,655,129 A | 4/1972 | Seiner | 239/60 |
| 4,062,649 A * | 12/1977 | Kuderna et al. | 436/104 |
| 4,293,095 A | 10/1981 | Hamilton et al. | 239/35 |
| 4,439,415 A | 3/1984 | Hennart et al. | 424/16 |
| 4,550,676 A | 11/1985 | Francis | 116/206 |
| 4,583,686 A | 4/1986 | Martens et al. | 239/35 |
| 4,629,330 A | 12/1986 | Nichols | 368/89 |
| 4,678,658 A | 7/1987 | Casey et al. | 424/7.1 |
| 4,793,988 A | 12/1988 | Casey et al. | 424/7.1 |
| 4,824,827 A | 4/1989 | Kelly et al. | 512/1 |
| 4,826,774 A | 5/1989 | Nagel | 436/106 |
| 4,921,636 A | 5/1990 | Traas | 252/408.1 |
| 4,952,401 A | 8/1990 | Hobbs | 424/405 |
| 4,965,063 A | 10/1990 | Casey et al. | 424/7.1 |
| 5,885,701 A | 3/1999 | Berman et al. | 428/212 |
| 6,534,079 B1 * | 3/2003 | Munagavalasa | 424/409 |
| 2003/0049410 A1 * | 3/2003 | Munagavalasa et al. | 428/137 |

FOREIGN PATENT DOCUMENTS

| EP | 0567018 A2 | 10/1993 | G01N/31/22 |
| JP | 7-324003 | 12/1995 | |
| WO | 00/69260 | 11/2000 | |

OTHER PUBLICATIONS

Patent Abstracts of Japan vol. 015, No. 067, (P–1167), Feb. 18, 1991 & JP 02 290592A Earth Chemical Corporation Nov. 30 1990 abstract.

Patent Abstracts of Japan vol. 2000, No. 13, Feb. 5 2001 & JP 2000 292563A Shintoo Fine KK, Oct. 20, 2000 abstract.

* cited by examiner

Primary Examiner—Lyle A. Alexander

(57) ABSTRACT

A time duration of end of product life indicator is disclosed which utilizes a volatile dye coated or impregnated into a substrate or carrier. The dye evaporates as a volatile component of the product evaporates thereby changing the color of the substrate or carrier. The consumer is alerted to the depletion of the volatile component of the product when the substrate or carrier changes from a colored or dyed state to an uncolored state. As a result, a visual time duration or end of product life indicator is provided.

22 Claims, 8 Drawing Sheets

US 6,790,670 B2

END OF USE AND TIME DURATION INDICATOR SYSTEM AND METHOD BASED ON VOLATILE DYE

TECHNICAL FIELD

The present invention relates generally to an end of product life indicator or a time duration indicator for products that include a volatile component. More specifically, the present invention relates to the use of a volatile dye as an end of product life indicator or a time duration indicator.

BACKGROUND ART

Substrates have been commonly used as carriers for air-treating compounds, such as insecticides, insect repellents, fragrances and deodorizing compounds. Insect repellent impregnated substrates and insecticide-impregnated substrates are useful in both residential and commercial settings to reduce or eliminate pests. Substrates impregnated with fragrances and deodorizing compounds are also useful in both residential and commercial settings to reduce or eliminate offensive odors and to provide a long-lasting pleasant odor. Volatile products may also be combined and impregnated into a substrate for combined purposes such as insect control and deodorization. A variety of different substrates are available and are known to those skilled in the art.

One disadvantage associated with the use of volatile components impregnated into a substrate is that the consumer is often unaware as to when the volatile component is depleted or exhausted. As a result, the consumer is unable to determine when to replace the product. The problem is compounded when the volatile product is a low odor or odor free insecticide. However, even when the volatile product is a fragrance or a deodorizing composition, consumers are often unable to determine when the product should be replaced for optimum product performance. Specifically, when relying upon the sense of smell, it is difficult to determine when a fragrance or a deodorizing component has been substantially depleted to a point where the product is no longer effective.

U.S. Pat. No. 4,921,636 teaches a visual indicator whereby the carrier or substrate is transparent or translucent when impregnated with a volatile product containing a solvent. As the solvent evaporates, the substrate or carrier becomes more opaque thereby providing a visual end of product life indicator for the consumer. However, this visual end of product life indicator is problematic because of the insufficient contrast between a light or white carrier and a partially transparent translucent carrier. A preferable indicator would include a sharp color change.

A color change indicator is disclosed in U.S. Pat. No. 4,824,827, assigned to the assignee of the present application. The color change taught in the '827 patent depends upon a pH change. The dye utilized is substantially non-volatile.

SUMMARY OF THE INVENTION

According to one aspect of the present invention, a time duration indicating system for a product that includes a volatile component comprises a substrate and a volatile dye. The substrate is coated with the volatile dye thereby coloring the substrate. As the volatile dye evaporates over time, the substrate changes color.

According to a further aspect of the present invention, a method for indicating an end of life for a product that includes a substrate impregnated with a volatile component comprises the step of coating a substrate with a volatile dye thereby coloring the substrate. As the volatile dye volatilizes over time, a color change of the substrate results.

According to yet another aspect of the present invention, an insecticide product with an end of life color change indicator includes a substrate and a volatile insecticide coated onto the substrate. The volatile insecticide is selected from the group consisting of transfluthrin, vapothrin, permethrin, prallethrin, tefluthrin and esbiothrin and guaiazulene is coated onto the substrate.

Other aspects and advantages of the present invention will become apparent upon consideration of the following detailed description.

DESCRIPTION OF THE PREFERRED EMBODIMENTS

Figure 1:
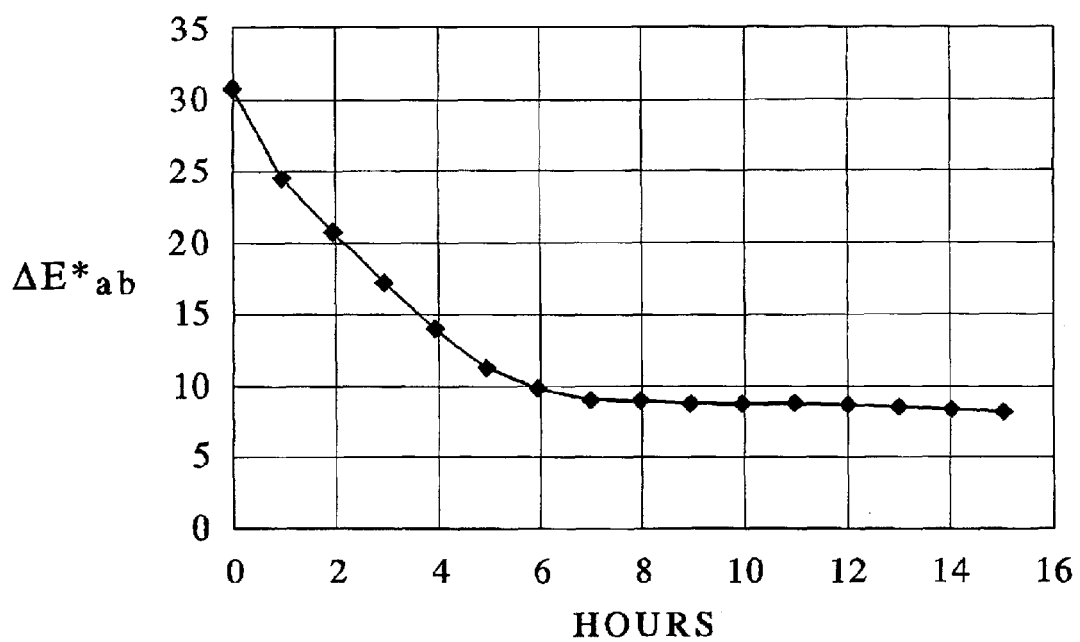
FIG. 1 illustrates, graphically, the data presented in Table 1 and, more specifically, a color change provided by an indicator system made in accordance with the disclosure after approximately 5.8 hours.

The present invention discloses the use of a volatile dye as a color change indicator for a product that includes a volatile component, such as a fragrance, odor treating chemical, insect repellent or insecticide. One preferred volatile dye is guaiazulene (1,4-dimethyl-7-(1-methylethylazulene). Other volatile dyes can be used with products and methods of the present invention. Guaiazulene is a blue oil that is know for its anti-inflammatory and anti-ulcerative properties. Once source of guaiazulene is Arcos Organics NV. (CAS) #489-84-9). Guaiazulene has a boiling point of 153° C. at 7.00 mm Hg. Guaiazulene is stable under normal temperatures and pressures. Upon initial application, guaiazulene imparts a blue color to a substrate and the blue color substantially fades or visually disappears as shown below.

It is preferable to dissolve the dye in an organic solvent. Use of the solvent as a carrier medium facilitates the application of the dye in a uniform manner to the substrate or carrier. The solvent can be polar or nonpolar and should be sufficiently volatile to evaporate during the process of drying after the application of the dye. Possible solvents include, but are not limited to, ISOPAR™ C, ISOPAR™ E, ISOPAR™ L, heptane, methanol, acetone, ethanol, isopropyl alcohol, dodecene and tetraydrofuran. ISOPAR™ C, ISOPAR™ E and ISOPAR™ L are hydrocarbon solvents of varying chain length and are available from Exxon Chemical Company.

The substrate or carrier can be fabricated from any material that is capable of absorbing the intermediate solution containing the dye. The absorption may take place take place either on the substrate or carrier surface or the substrate may be capable of being impregnated with the intermediate solution. The dye must be able to impart a color that is substantially different from the untreated substrate or carrier. The substrate must also allow for a free availability of the dye for slow evaporation when brought in contact with the ambient atmosphere. Examples of suitable substrate or carrier materials include, but are not limited to, cellulose, glass fiber filters, synthetic paper materials, ceramic materials, textiles, felt-type materials, wovens and nonwovens, bonded or sintered synthetic or natural polymer powders and the like.

Use of the terms "coated" or "coating" in connection with the application of the volatile dye is intended to cover adsorption, absorption, adhesion, impregnation, application or any other phenomenon that allows the volatile dye to be subsequently borne by the substrate or vaporize from the substrate.

In the data presented in the following Tables and Figures attached hereto, the substrate used was Whatman type 2 filter paper (catalogue no. 1002 240) which has a 8 $\mu$m pore size and is 7.5 mil thick. The filter paper was used in 1 inch circular discs. The paper was affixed to an inert heavy plastic base using conventional glue or cement. A computer controlled wind tunnel that is capable of achieving temperatures up to 40° C. and up to 8 m/s air velocities was used to test the effects of wind, speed and temperature on the indicator. It was found that guaiazulene, in a concentration of 50–500 $\mu$g/cm$^2$ on filter paper provided a suitable color change indicator.

A colorimeter was used to measure color change numerically. The L*a*b* color space (also referred to as CIELAB) was utilized. In this color space, L* indicates lightness and a* and b* are the chromaticity coordinates. The a* and b* indicate color directions: +a* is the red direction, –a* is the green direction, +b* is the yellow direction, and –b* is the blue direction. The center is achromatic; as the a* and b* values increase and moves out from the center, the saturation of the color increases.

Colorimeters are also widely used to detect color differences very accurately. In the L*a*b* color space, color difference can be expressed as a single numeric value, $\Delta E^*_{ab}$, which indicates the size of the color difference but not in what way the colors are different. $\Delta E^*_{ab}$ is defined by the following equation: $\Delta E^*_{ab}=[(\Delta L^*)^2+(\Delta a^*)^2+(\Delta b^*)^2]^{0.5}$.

In the following experiments, the color of a substrate impregnated with the same dye in time space as it is fading was recorded. During the process of fading, the L* (lightness) increases in value, the –b* value (blue color) decreases in value and approaches the origin (achromatic center) and the a* value remains predominantly unchanged. As a result, the $\Delta E^*_{ab}$ increases as the sample fades and hence accurately represents the color differences perceived by the human eye. The $\Delta E^*_{ab}$ value measured is with respect to a blank substrate since that is the color the substrate would eventually reach if all the dye evaporates and does not leave a residual color. It was observed that when $\Delta E^*_{ab}$ is 10 or less, the color of the substrate more or less resembles the blank substrate to a human eye and hence, a $\Delta E^*_{ab}$ value of 10 was selected as a depleted value. The $\Delta E^*_{ab}$ could go down for some indicators before it stabilizes at a constant value but a decrease below 10 is not noticeable to the human eye.

A Minolta CR-310 Chroma Meter is used for quantifying the color and measuring the color differences. It is a compact tristimulus color analyzer for measuring reflective colors of surfaces. This colorimeter has an 8 mm-diameter measuring area and uses diffuse illumination and a zero degrees viewing angle (specular component included). Absolute measurements are made in L*a*b* (CIE 1976) values.

In the following examples, at least three samples were considered for color measurements and the average values are reported.

EXAMPLE 1

Colorimeter Measurements on Indicators

Indicators were prepared by micropipetting 75 $\mu$L of 1 wt % dye solution in Ispoar E on 1 inch diameter circular Whatman type 2 (VWR Catalogue no. 1002 240) filter paper substrate. This corresponds to a dye surface density of 107 $\mu$g/cm$^2$. The samples were exposed in a wind tunnel at 1 m/s air velocity at a temperature of 26.6° C. While the sample was fading, calorimeter measurements were carried out and color difference from the untreated sample was calculated and shown in Table and FIG. 1. Results indicate that the initial color of the indicator is blue and slowly fades off with time until the final color reaches a plateau value that almost corresponds to that of untreated sample. The duration of the indicator as determined by a color difference value of 10 units from an undyed substrate is about 5.8 hours. This indicator system can be practically used to indicate the end-point of 5.8 hours in an environment with an air flow of 1 m/s and a temperature of 26.6° C.

TABLE 1

Colorimeter Measurements on Guaiazulene Dye Indicator System

| | |
|---|---|
| Air Velocity | 1 m/s |
| Temperature | 26.6° C. (80° F.) |
| Substrate | 1 in circular dia. Filter paper substrate |
| Intermediate Volume | 75 $\mu$L |
| Solvent | ISOPAR ™ E |
| Dye Level | 107 $\mu$g/cm$^2$ |

TABLE 1-continued

Colorimeter Measurements on Guaiazulene Dye Indicator System

| Sample | Hours | Color Space | Average of 6 readings | Std. Dev | $\Delta E^*_{ab}$ |
|---|---|---|---|---|---|
| Untreated Substrate | — | L* | 95.14 | 0.09 | 0.00 |
| | | a* | 0.02 | 0.02 | |
| | | b* | 0.54 | 0.01 | |
| Treated Substrate | 0 | L* | 70.96 | 0.71 | 30.77 |
| | | a* | 0.58 | 0.14 | |
| | | b* | −18.47 | 0.47 | |
| | 1 | L* | 75.10 | 0.49 | 24.48 |
| | | a* | −0.70 | 0.28 | |
| | | b* | −13.50 | 1.10 | |
| | 2 | L* | 77.52 | 0.93 | 20.80 |
| | | a* | −1.43 | 0.34 | |
| | | b* | −10.41 | 1.69 | |
| | 3 | L* | 79.96 | 1.44 | 17.16 |
| | | a* | −2.00 | 0.35 | |
| | | b* | −7.19 | 2.46 | |
| | 4 | L* | 82.19 | 1.86 | 13.89 |
| | | a* | −2.48 | 0.25 | |
| | | b* | −3.80 | 3.10 | |
| | 5 | L* | 84.27 | 1.45 | 11.29 |
| | | a* | −2.71 | 0.11 | |
| | | b* | −0.84 | 2.58 | |
| | 6 | L* | 85.87 | 1.20 | 9.73 |
| | | a* | −2.77 | 0.08 | |
| | | b* | 1.50 | 2.08 | |
| | 7 | L* | 87.16 | 0.89 | 8.94 |
| | | a* | −2.73 | 0.14 | |
| | | b* | 3.49 | 1.40 | |
| | 8 | L* | 87.73 | 0.84 | 8.89 |
| | | a* | −2.71 | 0.12 | |
| | | b* | 4.63 | 0.78 | |
| | 9 | L* | 88.09 | 0.81 | 8.73 |
| | | a* | −2.52 | 0.16 | |
| | | b* | 5.02 | 0.81 | |
| | 10 | L* | 88.52 | 0.77 | 8.72 |
| | | a* | −2.59 | 0.16 | |
| | | b* | 5.57 | 0.68 | |
| | 11 | L* | 88.70 | 0.78 | 8.72 |
| | | a* | −2.51 | 0.18 | |
| | | b* | 5.85 | 0.57 | |
| | 12 | L* | 88.94 | 0.77 | 8.63 |
| | | a* | −2.42 | 0.19 | |
| | | b* | 6.02 | 0.49 | |
| | 13 | L* | 89.20 | 0.86 | 8.48 |
| | | a* | −2.35 | 0.19 | |
| | | b* | 6.11 | 0.44 | |
| | 14 | L* | 89.41 | 0.86 | 8.29 |
| | | a* | −2.30 | 0.18 | |
| | | b* | 6.06 | 0.43 | |
| | 15 | L* | 89.52 | 0.79 | 8.12 |
| | | a* | −2.24 | 0.18 | |
| | | b* | 5.95 | 0.42 | |

EXAMPLE 2

Reproducibility of Indicator Duration in Lab Tests

Figure 2:
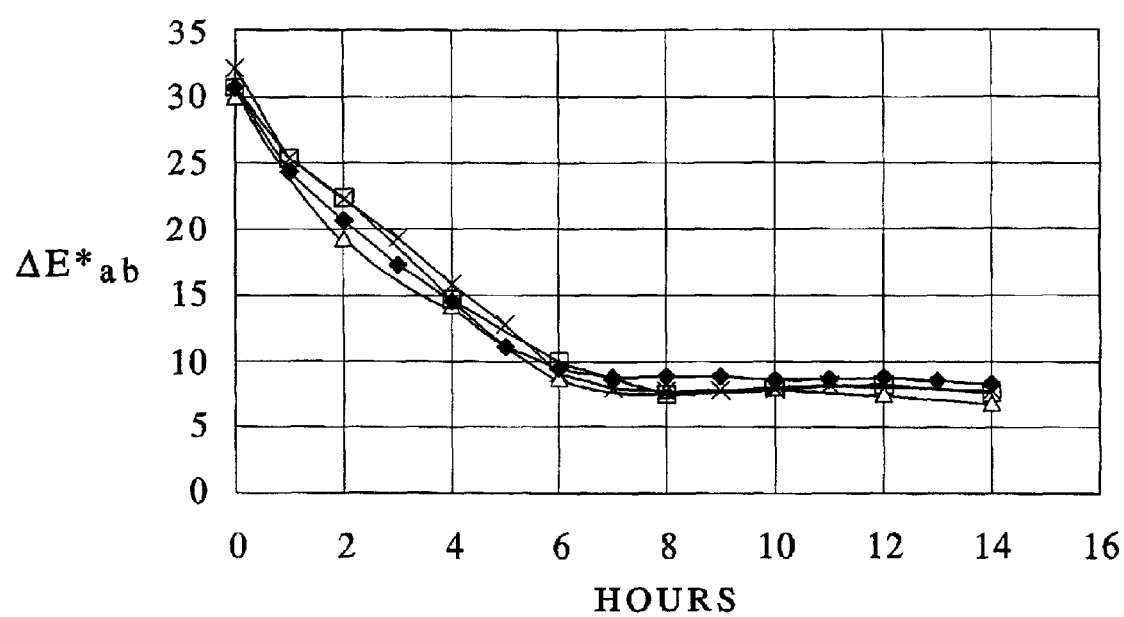
FIG. 2 illustrates, graphically, the performance of the indicator tested in Table 1 and FIG. 1 on subsequent days thereby illustrating the reproducibility of the data presented in Table 1 and FIG. 1.

Indicators used in Example 1 were subjected to testing under identical environmental conditions (temperature and air velocity) on four different days to check the reproducibility of the indicator duration in test conditions $\Delta E^*_{ab}$ values as a function of time for each of the four trials are shown in FIG. 2 and in Table 2. Results indicate that the experiments conducted in the wind tunnel are highly reproducible.

TABLE 2

Reproducibility of Indicator Duration

| Air Velocity | 1 m/s |
| Temperature | 26.6° C. (80° F.) |
| Substrate | 1 in circular dia. Filter paper substrate |
| Intermediate Volume | 75 µL |
| Solvent | ISOPAR ™ E |
| Dye Level | 107 µg/cm² |

| Hours | Trial #1 | Trial #2 | Trial #3 | Trial #4 |
|---|---|---|---|---|
| 0 | 30.8 | 30.85 | 30.15 | 32.32 |
| 1 | 24.5 | 25.55 | — | 25.46 |
| 2 | 20.8 | 22.46 | 19.46 | 22.33 |
| 3 | 17.2 | — | — | 19.41 |
| 4 | 13.9 | 14.75 | 14.14 | 15.96 |
| 5 | 11.3 | — | — | 12.76 |
| 6 | 9.7 | 10.11 | 8.72 | 8.84 |
| 7 | 8.9 | — | — | 8.00 |
| 8 | 8.9 | 7.84 | 7.79 | 7.73 |
| 9 | 8.7 | — | — | 7.85 |
| 10 | 8.7 | 8.14 | 8.20 | 7.94 |
| 11 | 8.7 | — | — | 8.15 |
| 12 | 8.6 | 8.04 | 7.64 | — |
| 13 | 8.5 | — | — | — |
| 14 | 8.3 | 7.76 | 7.05 | — |

EXAMPLE 3

Effect of Dye Concentration on Indicator Duration

Figure 3:
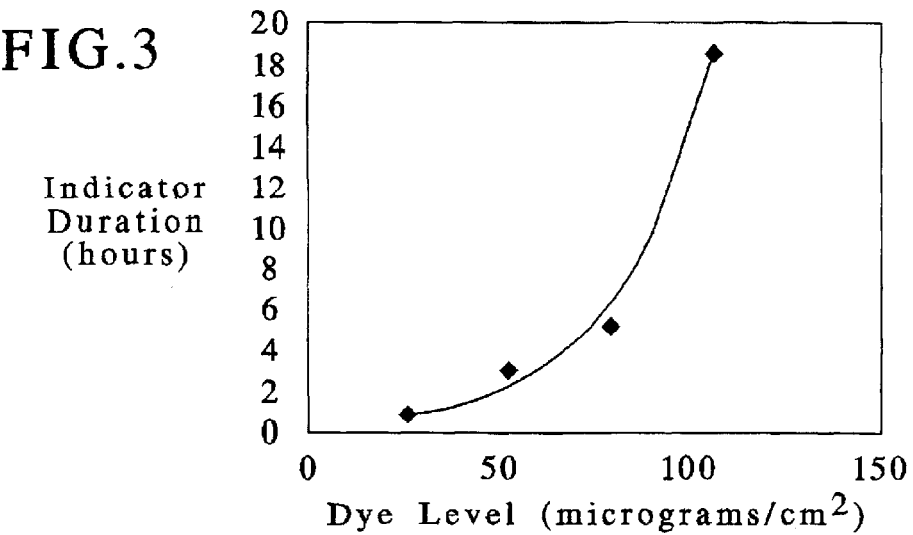
FIG. 3 illustrates, graphically, the data of Table 3 and, more particularly, the effect of dye concentration on indicator duration.

Four different dye levels with surface densities ranging from 26.6 µg/cm² to 107 µg/cm² were tested in the wind tunnel at 32.2° C. at 1 m/s air velocity and indicator durations were determined. Results, as shown in Table 3 and FIG. 3, indicate that the indicator duration uniquely depends on the dye level and it increases with dye level. Thus, indicators with specific duration can be prepared by applying an appropriate level of dye.

TABLE 3

Effect of Dye Level on Indicator Duration

| Substrate | 1 in diameter Filter paper |
| Intermediate Volume | 75 µL |
| Solvent | ISOPAR ™ E |
| Temperature | 32.2° C. (90° F.) |
| Air Velocity | 1 m/s |

| Dye Level | Indicator Duration (hours) |
|---|---|
| 26.6 µg/cm² | 0.8 |
| 53.3 µg/cm² | 3.1 |
| 79.9 µg/cm² | 5.4 |
| 107 µg/cm² | 18.7 |

EXAMPLE 4

Effect of Retarder on Indicator Duration

A retarder can be added to the intermediate solution to "tune" the indicator duration. Any relatively low volatile organic chemical that is chemically compatible can be used as a retarder. A retarder usually retards the evaporation of the dye and thus prolongs the indicator duration. The extent of prolonging the end point depends on the type of the retarder utilized. Some retarders prolong the endpoint to as many at 18 hours while others do not significantly affect the indicator duration. Table 4 illustrates the effect of some of the retarders on the indicator duration. As shown in Tables 5, 6 and 7 and FIGS. 4–6, respectively, increasing the retarder surface density on the substrate at the same dye level increases the indicator duration. Adding two parts of retarder for each part of dye extended the indicator duration by as much as a factor of three as shown in Tables 5, 6 and 7. Surprisingly, the indicator duration is directly proportional to the amount of retarder used in the system (compare with Table 3 which illustrates the rapid increase in indicator duration with dye level).

TABLE 4

Effect of Retarder Type on Indicator Duration

| Substrate | 1 in diameter Filter paper |
|---|---|
| Intermediate Volume | 75 µL |
| Solvent | ISOPAR ™ E |
| Dye Level | 107 µg/cm$^2$ |
| Retarder Level | 213 µg/cm |
| Temperature | 26.6° C. (80° F.) |
| Air Velocity | 1 meter/second |

| Retarder Type | Indicator Duration (hours) |
|---|---|
| None | 5.8 |
| Hexadecane | 5.5 |
| Tetradecene | 5.6 |
| Dodecene | 8.3 |
| Deet | 9.9 |
| Vapothrin | 14.0 |
| Permethrin | 14.0 |
| Prallethrin | 15.9 |
| Tefluthrin | 17.0 |
| Esbiothrin | 17.7 |

Figure 4:
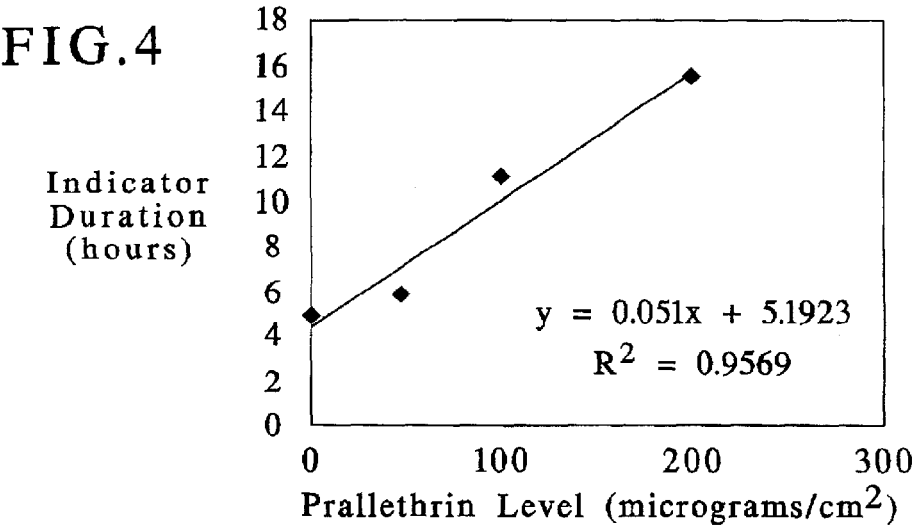
FIG. 4 illustrates, graphically, the data of Table 5 and, more particularly, the effect of prallethrin concentration as a retarder on indicator duration.

The results of Table 5 are shown graphically in FIG. 4.

TABLE 5

Effect of Prallethrin Level on Indicator Duration

| Substrate | 1 in diameter Filter paper |
|---|---|
| Intermediate Volume | 75 µL |
| Solvent | ISOPAR ™ E |
| Dye Level | 107 µg/cm$^2$ |
| Temperature | 26.6° C. (80° F.) |
| Air Velocity | 1 meter/second |

| Prallethrin Surface Density | Indicator Duration (hours) |
|---|---|
| 0.0 µg/cm$^2$ | 5.7 |
| 53.3 µg/cm | 6.6 |
| 107 µg/cm$^2$ | 11.6 |
| 213 µg/cm$^2$ | 15.9 |

Figure 5:
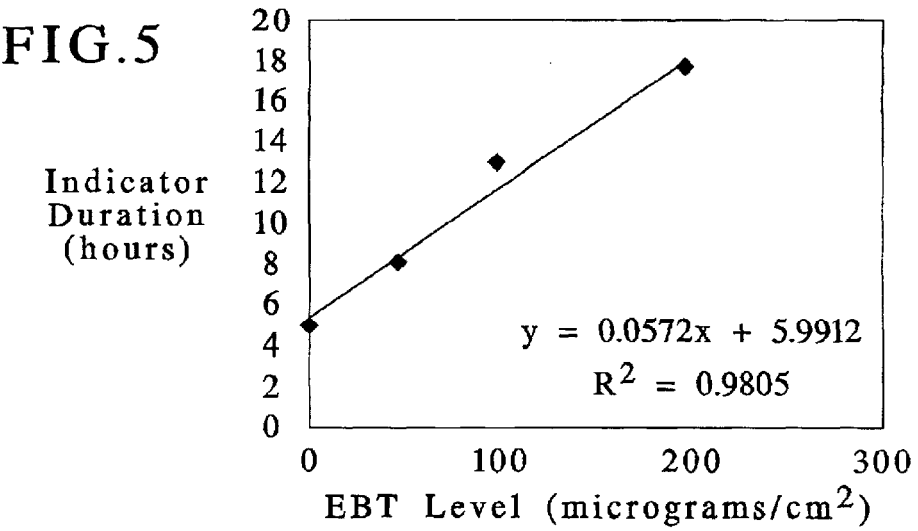
FIG. 5 illustrates, graphically, the data of Table 6 and, more particularly, the effect of esbiothrin concentration as a retarder on indicator duration.

The results of Table 6 are shown graphically in FIG. 5.

TABLE 6

Effect of Esbiothrin Level on Indicator Duration

| Substrate | 1 in diameter Filter paper |
|---|---|
| Intermediate Volume | 75 µL |
| Solvent | ISOPAR ™ E |
| Dye Level | 107 µg/cm$^2$ |
| Temperature | 26.6° C. (80° F.) |
| Air Velocity | 1 meter/second |

| Esbiothrin Surface Density | Indicator Duration (hours) |
|---|---|
| 0.0 µg/cm$^2$ | 5.7 |
| 53.3 µg/cm$^2$ | 8.7 |
| 107 µg/cm$^2$ | 13.2 |
| 213 µg/cm$^2$ | 17.7 |

TABLE 7

Effect of Transfluthrin Level on Indicator Duration

| Substrate | 1 in diameter Filter paper |
|---|---|
| Intermediate Volume | 75 µL |
| Solvent | ISOPAR ™ E |
| Dye Level | 107 µg/cm$^2$ |
| Temperature | 26.6° C. (80° F.) |
| Air Velocity | 1 meter/second |

| Transfluthrin Surface Density | Indicator Duration (hours) |
|---|---|
| 0.0 µg/cm$^2$ | 5.7 |
| 53.3 µg/cm$^2$ | 8.5 |
| 107 µg/cm$^2$ | 14.5 |

Figure 6:
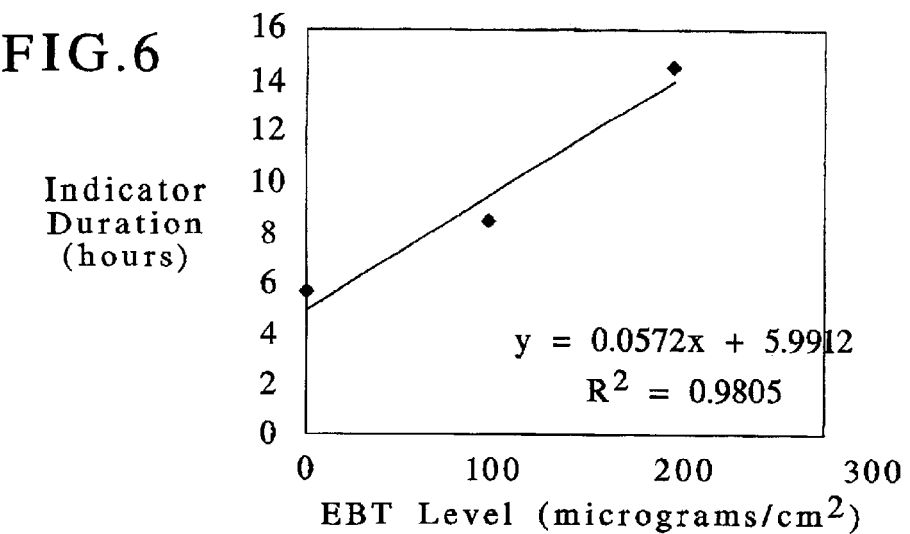
FIG. 6 illustrates, graphically, the data of Table 7 and, more particularly, the effect of transfluthrin concentration as a retarder on indicator duration.

The results of Table 7 are shown graphically in FIG. 6.

EXAMPLE 5

Effect of Solvent on Indicator Duration

The solvent, being high volatile relative to the dye, is expected to evaporate rapidly during the drying process leaving the dye behind to evaporate more slowly at a later period. However, contrary to our expectations, Table 8 illustrates that the type of solvent used to apply the dye on the substrate can have a strong influence on the indicator duration. Solvents with high Hansen polar solubility component appear to lead to significantly prolonged indicator duration as opposed to those that are relatively non-polar in nature. This dependence is again attributed to chemical interactions that are present between the dye and the solvent.

TABLE 8

Effect of Solvent on Indicator Duration

| Substrate | 1 in diameter Filter paper |
|---|---|
| Intermediate Volume | 75 µL |
| Solvent | ISOPAR ™ E |
| Dye Level | 107 µg/cm$^2$ |
| Temperature | 26.6° C. (80° F.) |
| Air Velocity | 1 meter/second |

| Solvent | Indicator Duration (hours) |
|---|---|
| Isobutyl Acetate | 5.3 hours |
| Acetone | 8.0 hours |
| Methanol | 10.9 hours |
| IPA | 13.3 hours |
| Ethanol | 12.5 hours |
| ISOPAR ™ E | 5.7 hours |

EXAMPLE 6

Effect of Air Velocity on Indicator Duration

Figure 7:
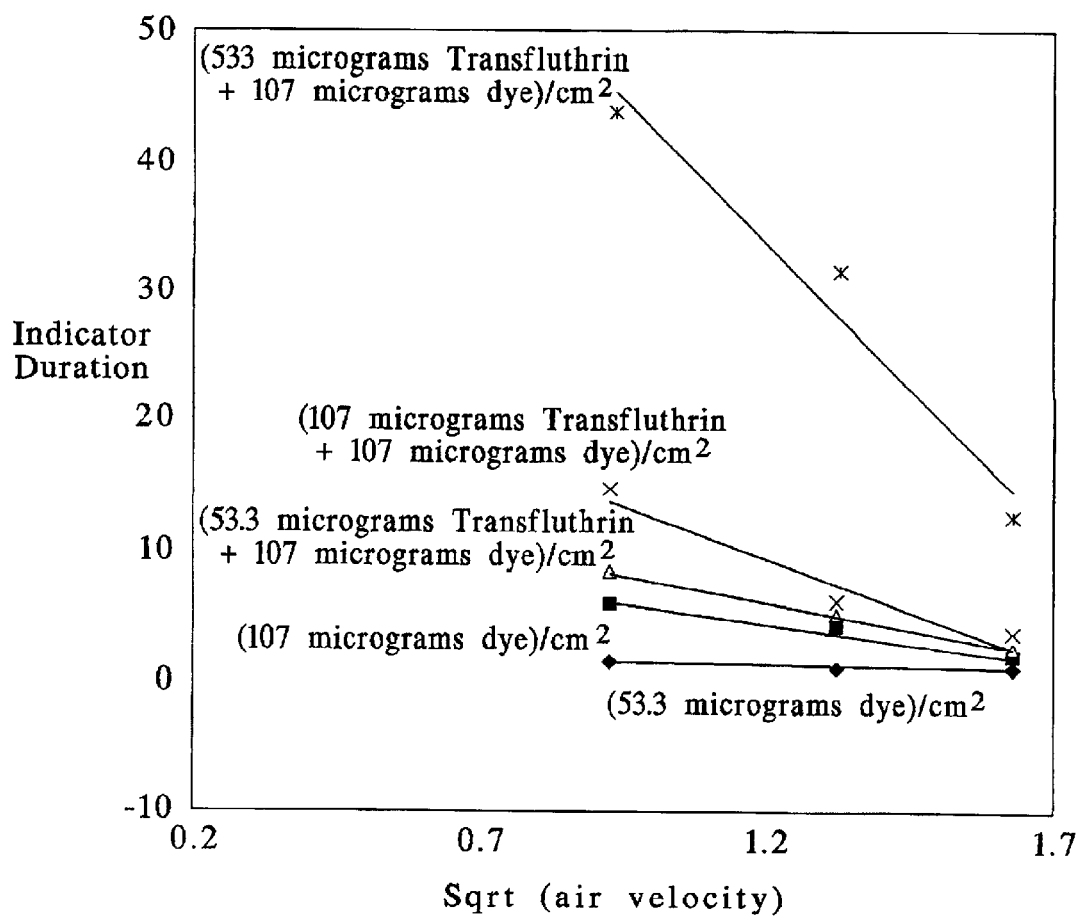
FIG. 7 illustrates, graphically, the data presented in Table 9 and, more specifically, the effect of air velocity on indicator duration.

Increasing air velocity decreases the indicator duration as show in Table 9 and FIG. 7 for indicator systems with and without retarders. This is expected since increasing air velocity accelerates the evaporation rate of the dye as well as the retarder.

TABLE 9

Effect of Air Velocity on Indicator Duration

| Substrate | 1 in diameter Filter paper |
|---|---|
| Intermediate Volume | 75 µL |
| Solvent | ISOPAR ™ E |
| Temperature | 26.6° C. (80° F.) |

TABLE 9-continued

Effect of Air Velocity on Indicator Duration

| | Indicator Duration (hours) | | |
|---|---|---|---|
| Indicator System | V = 1 m/s | V = 3 m/s | V = 6 m/s |
| 53.3 µg/cm² $^{Dye}$ Dye | 1.7 | 1.0 | 0.9 |
| 107 µg/cm² Dye | 5.8 | 3.9 | 1.8 |
| 107 µg/cm² Dye + 53.3 µg/cm² Transfluthrin | 8.5 | 4.9 | 2.7 |
| 107 µg/cm² Dye + 107 µg/cm² Transfluthrin | 14.5 | 5.9 | 3.8 |
| 107 µg/cm² Dye + 533 µg/cm² Transfluthrin | 43.9 | 31.5 | 12.6 |

EXAMPLE 7

Effect of Temperature on Indicator Duration

Figure 8:
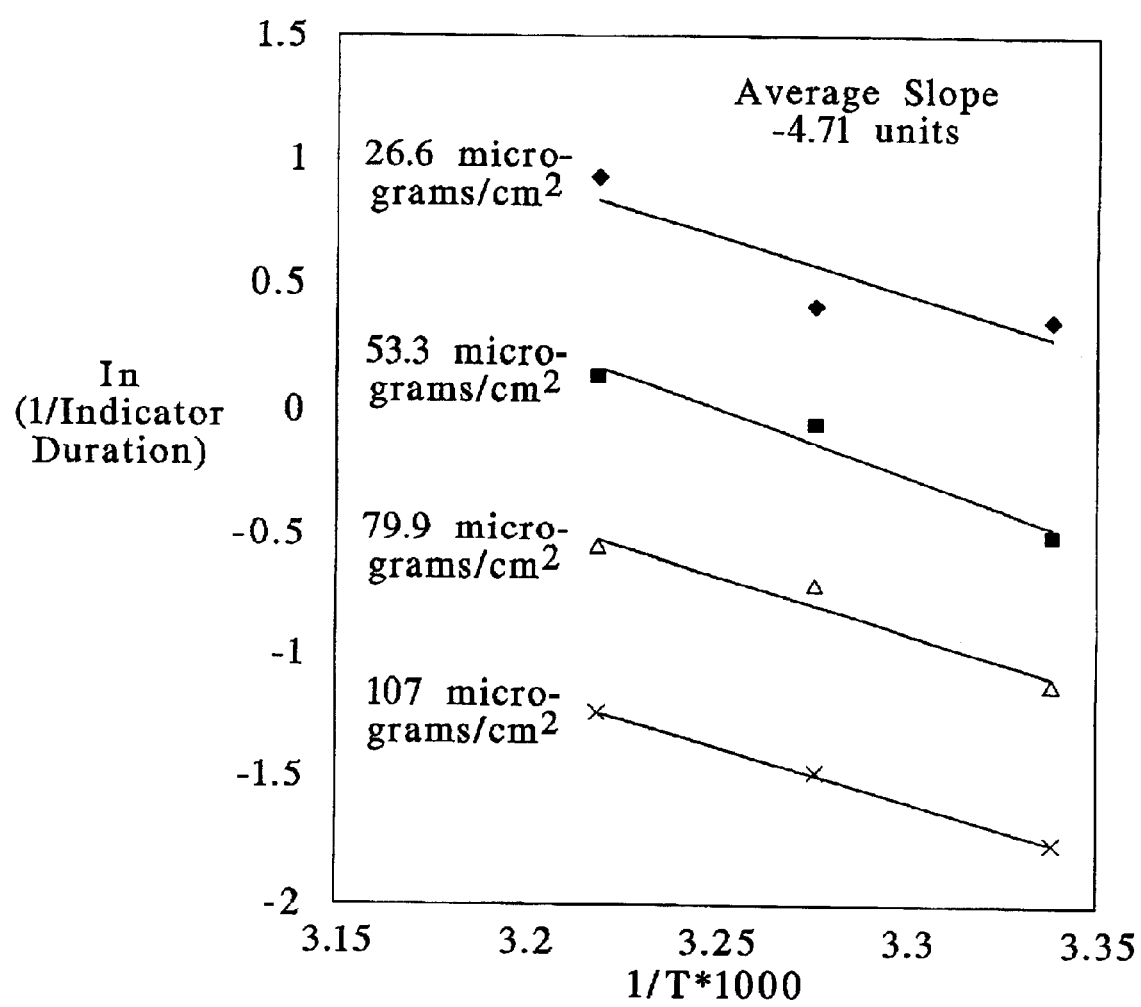
FIG. 8 illustrates, graphically, the data presented in Table 10 and, more specifically, the effect of air temperature on indicator duration without the presence of a retarder, such as an insecticide.
Figure 9:
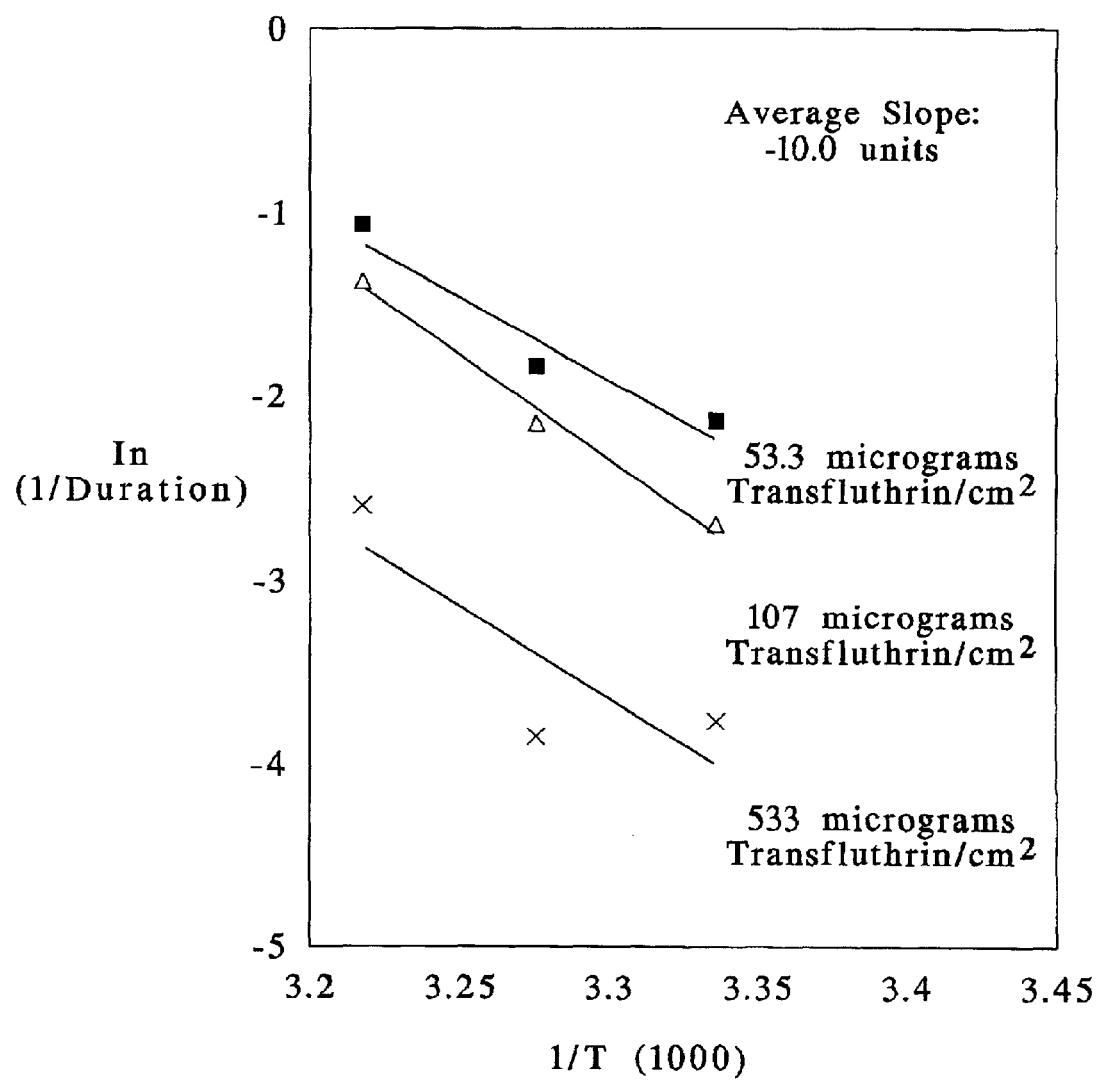
FIG. 9 illustrates, graphically, the data of Table 11 and, more specifically, the effect of temperature on indicator duration with transfluthrin included as a retarder.
Figure 10:
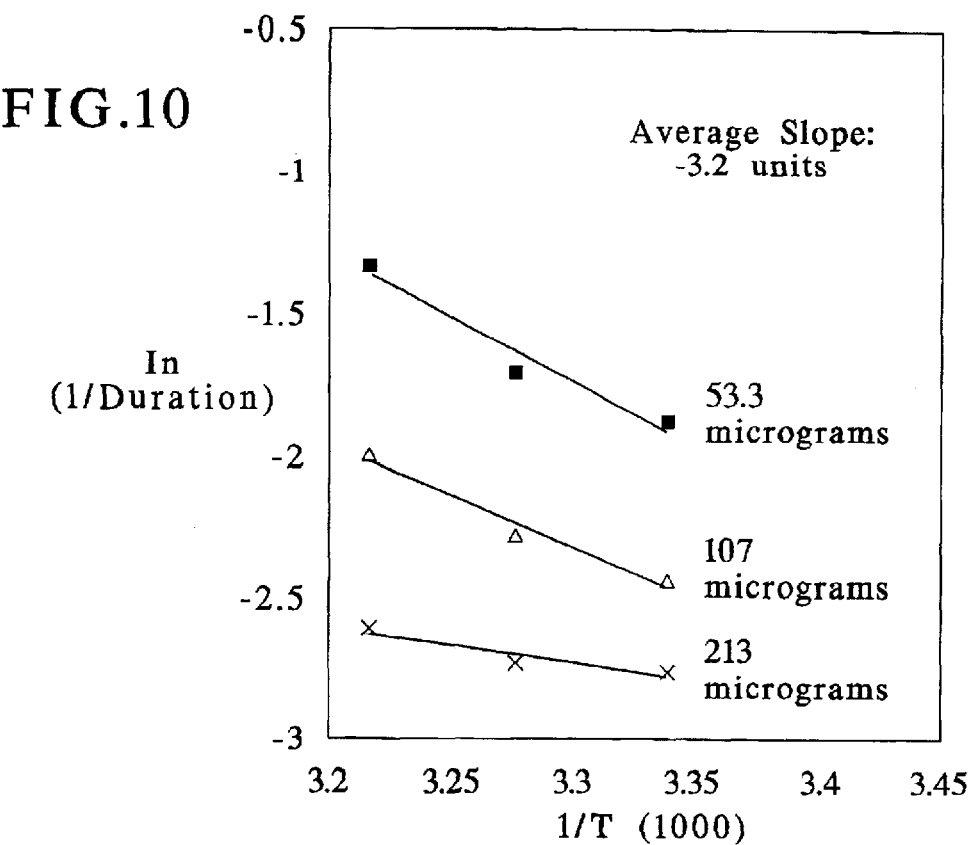
FIG. 10 illustrates, graphically, the data of Table 12 and, more specifically, the effect of temperature on indicator duration with prallethrin included as a retarder.
Figure 12:
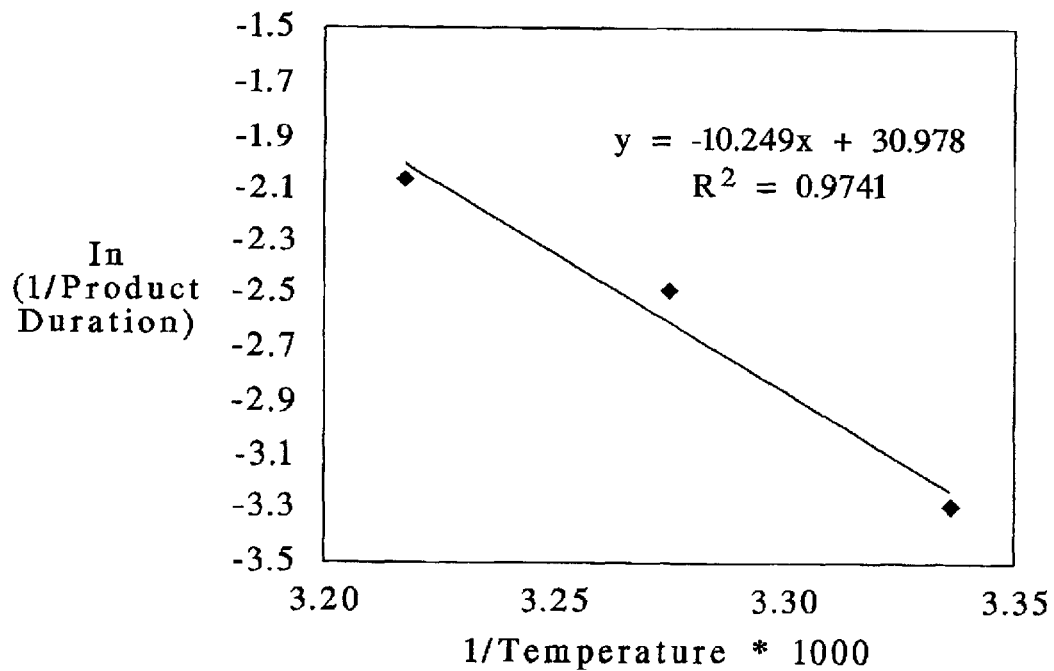
FIG. 12 illustrates, graphically, the data presented in Table 16 and, more specifically, the rate of evaporation of transfluthrin from an inert plastic substrate.
Figure 11:
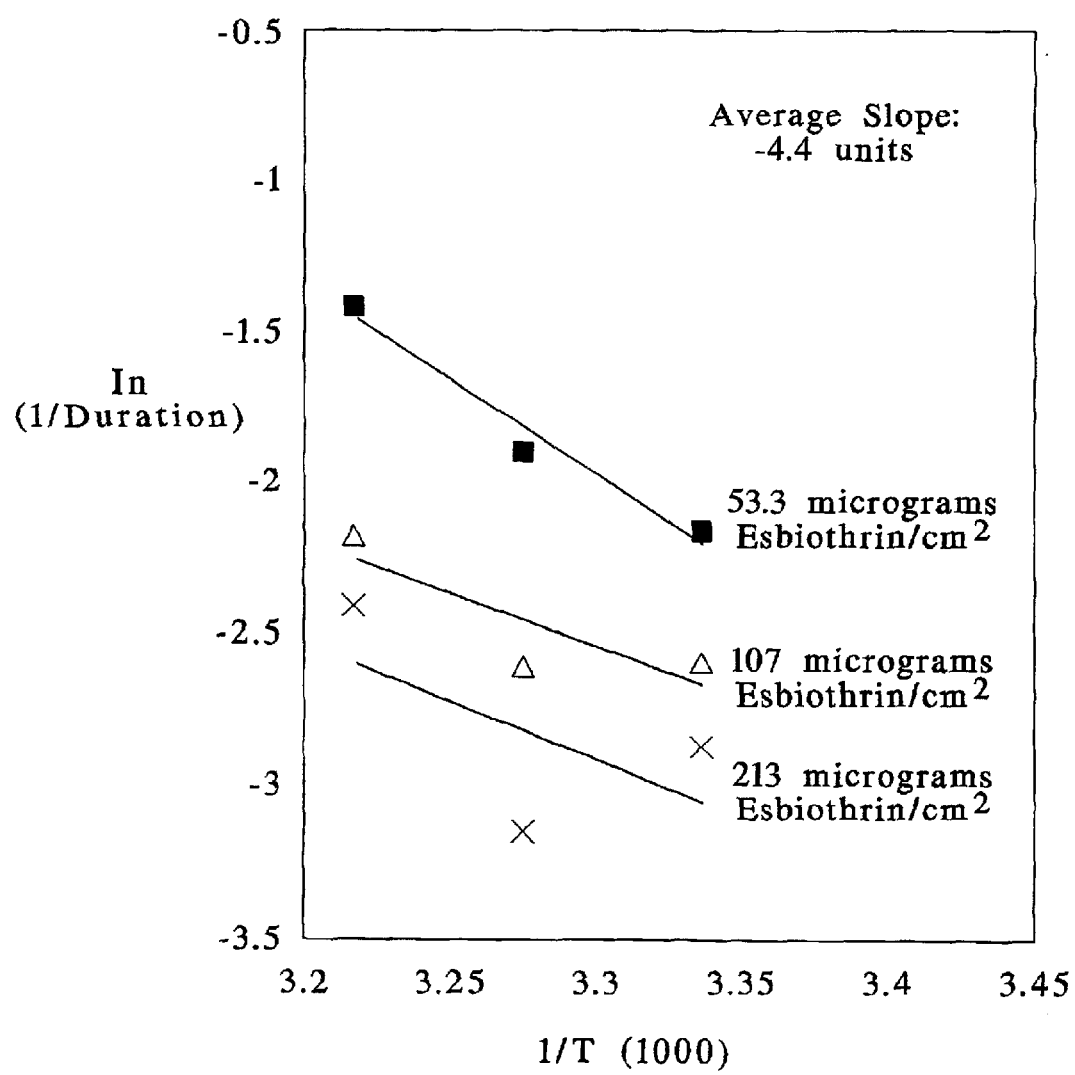
FIG. 11 illustrates, graphically, the data of Table 13 and, more specifically, the effect of temperature on indicator duration with esbiothrin included as a retarder.

Tables 10–13 and FIGS. 8–11, respectively, show the effect of temperature on indicator duration for indicator systems without retarder (Table 10; FIG. 8), with Transfluthrin as a retarder (Table 11; FIG. 9), with Prallethrin as a retarder (Table 12; FIG. 10), with Esbiothrin as a retarder (Table 13; FIG. 11). Clearly, there is a general trend of indicating decreasing indicator durations with increasing ambient temperatures.

TABLE 10

Effect of Temperature on Indicator Duration Without Retarder

| Substrate | 1 in diameter Filter paper |
| Intermediate Volume | 75 µL |
| Solvent | ISOPAR ™ E |
| Air Velocity | 1 m/s |

| | Indicator Duration | | |
|---|---|---|---|
| Dye Surface Density | T = 26.6° C. | T = 32.2° C. | T = 37.7° C. |
| 26.6 µg/cm² | 0.7 | 0.67 | 0.4 |
| 53.3 µg/cm² | 1.7 | 1.08 | 0.9 |
| 79.9 µg/cm² | 3.1 | 2.1 | 1.8 |
| 107 µg/cm² | 5.8 | 4.38 | 3.5 |

TABLE 11

Effect of Temperature on Indicator Duration With Transfluthrin as Retarder

| Substrate | 1 in diameter Filter paper |
| Intermediate Volume | 75 µL |
| Solvent | ISOPAR ™ E |
| Dye Level | 107 µg/cm² |
| Air Velocity | 1 m/s |

| | Indicator Duration (hours) | | |
|---|---|---|---|
| Transfluthrin Level | T = 26.6° C. | T = 32.2° C. | T = 37.7° C. |
| 53.3 µg/cm² | 8.5 | 6.2 | 2.9 |
| 107 µg/cm² | 14.5 | 8.4 | 3.8 |
| 553 µg/cm² | 43.9 | 47.0 | 13.3 |

TABLE 12

Effect of Temperature on Indicator Duration With Prallethrin as Retarder

| Substrate | 1 in diameter Filter paper |
| Intermediate Volume | 75 µL |
| Solvent | ISOPAR ™ E |
| Dye Level | 107 µg/cm² |
| Air Velocity | 1 m/s |

| | Indicator Duration (hours) | | |
|---|---|---|---|
| Prallethrin Surface Density | T = 26.6° C. | T = 32.2° C. | T = 37.7° C. |
| 53.3 µg/cm² | 6.6 | 5.5 | 3.8 |
| 107 µg/cm² | 11.6 | 9.9 | 7.4 |
| 213 µg/cm² | 15.9 | 15.5 | 13.8 |

TABLE 13

Effect of Temperature on Indicator Duration With Esbiothrin as Retarder

| Substrate | 1 in diameter Filter paper |
| Intermediate Volume | 75 µL |
| Solvent | ISOPAR ™ E |
| Dye Level | 107 µg/cm² |
| Air Velocity | 1 m/s |

| | Indicator Duration (hours) | | |
|---|---|---|---|
| Esbiothrin Surface Density | T = 26.6° C. | T = 32.2° C. | T = 37.7° C. |
| 53.3 µg/cm² | 8.7 | 6.7 | 4.1 |
| 107 µg/cm² | 13.2 | 13.4 | 8.8 |
| 213 µg/cm² | 17.7 | 23.5 | 11.2 |

Tables 14 and 15 illustrate the effect of temperature on systems with different solvents (Table 14) and different retarders (Table 15).

TABLE 14

Effect of Temperature on Indicator Duration With Different Solvents

| Substrate | 1 in diameter Filter paper |
| Intermediate Volume | 75 µL |
| Dye Level | 107 µg/cm² |

| | Indicator Duration (hours) | | |
|---|---|---|---|
| Solvent | T = 22.2° C. V = 0 m/s | T = 26.6° C. V = 1 m/s | T = 32.2° C. V = 1 m/s |
| Isobutyl Acetate | 18.7 | 5.3 | 4.0 |
| Acetone | 29.3 | 8.0 | 6.0 |
| Methanol | n/a* | 10.9 | 11.0 |
| IPA | n/a* | 13.3 | n/a* |
| Ethanol | n/a* | 12.5 | 14.3 |
| ISOPAR ™ E | n/a* | 5.7 | 4.6 |

*The color difference never reached a value of 10 during exptl. Time.

TABLE 15

Effect of Temperature on Indicator Duration for Different Retarders

| Substrate | 1 in diameter Filter paper |
| Intermediate Volume | 75 µL |
| Solvent | ISOPAR ™ E |
| Dye Level | 107 µg/cm² |
| Retarder Level | 213 µg/cm² |

TABLE 15-continued

| Effect of Temperature on Indicator Duration for Different Retarders | | | |
|---|---|---|---|
| | Indicator Duration (hours) | | |
| Retarder Type | T = 22.2° C. V = 0 m/s | T = 26.6° C. V = 1 m/s | T = 32.2° C. V = 1 m/s |
| None | n/a* | 5.8 | 4.6 |
| Hexadecane | 16.2 | 5.5 | 4.9 |
| Tetradecene | 10.4 | 5.6 | 3.4 |
| Transfluthrin | 27.9 | 7.2 | 21.8 |
| Dodecene | 11.3 | 8.3 | 3.5 |
| Deet | 56.8 | 9.9 | 7.0 |
| Vapothrin | 46.0 | 14.0 | 8.0 |
| Permethrin | n/a* | 14.0 | 15.4 |
| Prallethrin | n/a* | 15.9 | 21.1 |
| Tefluthrin | n/a* | 17.0 | 18.3 |
| Esbiothrin | n/a* | 17.7 | 23.5 |

*The color difference never reached a value of 10 during exptl. Time.

EXAMPLE 8

Sensitivity to Ambient Conditions

Table 3 and FIG. 3 illustrate that the indicator duration is not linearly related to the level of dye while Tables 5–7 and FIGS. 4–6, respectively, suggest the linearity of indicator duration with the level of retarder present in the indicator system.

There are many systems whose performance depends on evaporation of a chemical from an impregnated substrate such as insecticidal strip or a fragrance strip. The parameters that affect the evaporation of such an active are primarily temperature of the surroundings, and velocity of air blowing over the system. It has been proven in chemical engineering literature that, for such a system, evaporation rate of the active is directly proportional to the square root of the velocity of the air blowing over the system. In addition, pure components typically follow the Clausius-Clapeyron equation, which states that the natural logarithm of vapor pressure is directly proportional to the inverse of absolute temperature. Since evaporation rate is directly proportional to the vapor pressure, it can be deduced that the evaporation rate is also related to temperature in a similar fashion for pure components. Intuitively, it appears that product life is inversely related to evaporation rate. The higher the evaporation rate, the lower will be the product life. In fact, it can be proven mathematically that product life is inversely proportional to the evaporation rate. Also, again, on intuitive grounds, it said that product life is directly proportional to the total amount of active available for evaporation. Based on these reasoning, it is concluded that, for pure component systems:

(a) product life is directly proportional to the amount of active present in the system;

(b) product life is inversely proportional to the square root of the velocity of air blowing over the system; and (c) natural logarithm of the inverse of product life is directly proportional to the inverse of absolute temperature.

Keeping the above correlations in mind, we will now see how the indicator duration is influenced by the retarder level or dye level present in the indicator system, ambient air velocity, and temperature.

Table 3 illustrates that the indicator duration is not linearly related to the level of dye while tables 5, 6, and 7 suggest the linearity of indicator duration with the level of retarder present in the indicator system. Thus, the indicator system responds in the same manner that the passive evaporation product responds to the dose level. Both indicator duration and product life are directly proportional to active level.

Table 9 and FIG. 7 illustrate that the indicator duration is inversely proportional to the square root of the air velocity as illustrated by a negative slope suggesting that the indicator duration also responds in the same manner the product does to the air velocity. When air velocity increases, product duration decreases and indicator duration also decrease by the same extent.

In Tables 10 and 11, and FIGS. 8–9, respectively, the natural logarithm of inverse of indicator duration (which correlates with natural logarithm of evaporation rate of the dye) is plotted as a function of inverse of absolute temperature. For system containing pure dye, the regressed lines are linear and parallel to each other. The linear nature of the lines suggests that the dye system follows the Clausius-Clapeyron equation, which is derived from thermodynamic fundamentals. The parallel nature of the lines confirm the accuracy of the experiments once again since the slope depends only on the type of chemical used on the substrate but not on the amount of chemical used. Since the same dye is used at different levels in Table 10 and FIG. 8, the lines are expected to be parallel to each other. In the former case, the slope corresponds uniquely to the dye where as in the latter case, the slope corresponds primarily to the retarder since the retarder is the determining factor for the indicator duration. A similar plot is shown in Table 11 and FIG. 9 for a constant level of dye and different levels of Transfluthrin. All lines are linear and are parallel to each other suggesting that the dye and retarder system behaves like a single component system. The mixture, at different compositions of dye and retarder, behaving as a single component is unexpected.

In an unrelated experiment, 5 mg of Transfluthrin coated on a plastic substrate having dimensions of 2"×8" was placed in a wind tunnel and maintained at an air velocity of 5 m/s and an air temperature of 80° F. The Transfluthrin was thereafter allowed to evaporate for six hours. The strip was then removed from the wind tunnel and evaluated to determine the residual unevaporated amount remaining on the strip. Based on this, average evaporation loss per hour was determined. Product life was then estimated based on the knowledge that 5 mg of active was placed on the strip at the start. The experiment was repeated at 90° F. and 100° F. air temperatures. The logarithm of the inverse of product life was plotted as a function of the inverse of absolute temperature. The regressed line was a straight line with a negative slope suggesting that the evaporation of Transfluthrin from a plastic strip follows the Clausius-Clapeyron equation, which was to be expected inasmuch as the samples comprised a uniformly evaporating single component. While the slope of the regressed line was −10.2 units (see Table 16 and FIG. 12), the slope of a similarly regressed line from a dye with Transfluthrin as a retarder system (see Table 11 and FIG. 9) was −10.0 units. These slopes can be considered identical within the range of experimental error. However, for the indicator system without a retarder, the average slope was −4.7 units, which is quite different than the above two slopes. As shown in Tables 12 and 13 and FIGS. 10 and 11, respectively, the average slopes for Prallethrin and Esbiothrin are −3.2 units and −4.4 units, which are, again, quite different from that of Transfluthrin. This suggests that the indicator with Transfluthrin as a retarder responds to temperature in the same manner that a passive evaporating system with Transfluthrin would. The dye and Transfluthrin mixture behaves more like pure Transfluthrin in terms of the vapor pressure dependency thereof on temperature (instead of displaying an intermediate behavior).

In summary, for a passively evaporating product that contains a slowly evaporating chemical, an indicator system can be chosen utilizing the same evaporating chemical as a retarder to indicate the end point of the product. Surprisingly, both the product and the indicator system in such a composition responds in exactly the same fashion to variations in the ambient temperature and air velocity, and hence, the indicator system continues to indicate the end point of the product irrespective of variations in ambient conditions. This is because the rate at which the indicator system loses the retarder strongly correlates to the rate at which the active evaporates from the product at any temperature and air flow that the product might be subjected to.

TABLE 16

Transfluthrin Evaporation From an Inert Plastic Substrate

| Temperature (° F.) | Velocity (m/s) | 6 hr Release (mg) | Product Life |
|---|---|---|---|
| 80 | 5 | 1.13 | 26.5 |
| 90 | 5 | 2.5 | 12.0 |
| 100 | 5 | 3.83 | 7.8 |

EXAMPLE 9

Stability of Indicator Samples

Dye samples with and without retarder that were used in all the above examples were prepared and color measurements were noted. The samples were then sandwiched between two transparent glass sheets. The edges of the glass plates were glued together hermetically using rubber cement. A total of three sets of experimental samples were prepared of which, one set was exposed on the bench top at 72° F., the second set was kept in the over at 130° F., and the third set was stored in a refrigerator at 32° F. The difference in color between the period, as measured by the quantity $\Delta E^*_{ab}$ was measured and shown in Table 17. As shown, the samples stored at or below room temperature are sufficiently stable compared to those stored at higher temperature.

TABLE 17

Stability Results

| Substrate | 1 in diameter Filter paper |
|---|---|
| Intermediate Volume | 75 µL |
| Solvent | ISOPAR ™ E |
| Dye Level | 107 µg/cm² |
| Retarder Level | 213 µg/cm² |

| | $E_{ab}$ | | | | | |
|---|---|---|---|---|---|---|
| | 32 deg. F. | | 72 deg. F. | | 130 deg. F. | |
| Retarder Type | 0 days | 1 month | 1 day | 1 | 0 days | 1 |
| No Retarder | 29.6 | 28.5 | 26.8 | 22.5 | 28.7 | 19.4 |
| 2% Transfluthrin | 34.5 | 31.3 | 35.7 | 26.9 | 33.7 | 23.2 |
| 2% Etoc | 35.1 | 32.6 | 34.9 | 25.9 | 35.2 | 22.5 |
| 2% EBT | 29.7 | 26.8 | 31.9 | 25.6 | 32.9 | 22.9 |
| 2% Vapothrin | 29.6 | 32.3 | 31.5 | 28.4 | 32.2 | 16.2 |

Figure 13:
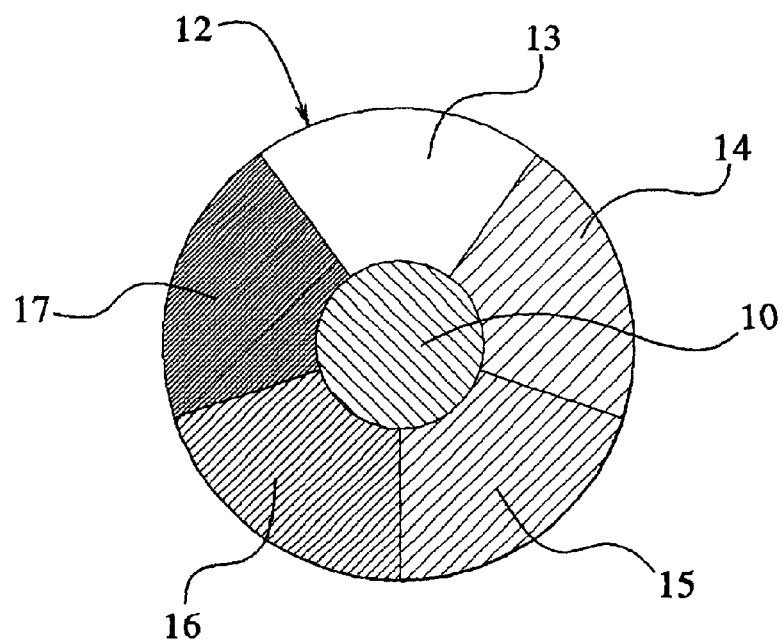
FIG. 13 is a plane view of a color change indicator and reference template.
Figure 14:
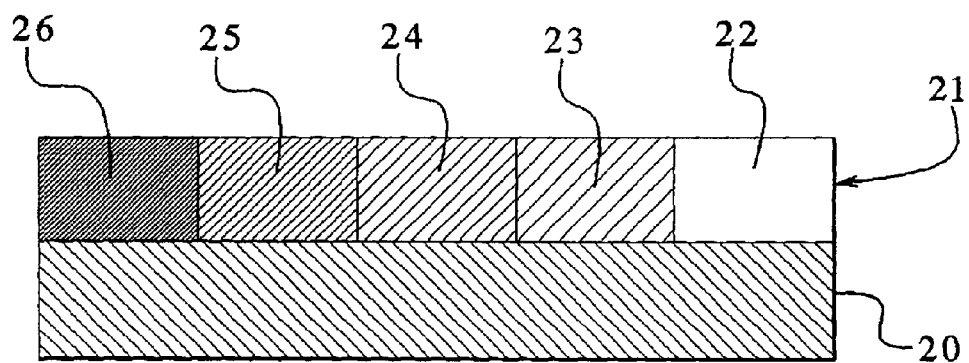
FIG. 14 is a plane view of another color change indicator and reference template.

FIG. 13 illustrates an embodiment where a color change indicator 10 made in accordance with the principles discussed above is surrounded by a reference template 12 divided into five sections 13–17. The section 17 is indicative of the darkness of the indicator 10 when the indicator 10 is freshly coated with the volatile dye. Section 16 is indicative of the color of the indicator 10 when a portion of the dye has evaporated, such as approximately 25%. Thus, section 16 provides a color reference for an indicator that has approximately 75% of its dye (and therefore product) unvolatilized. Sections 15, 14 and 13 are all progressively lighter in hue and are indicative of the color of the indicator 10 when it has approximately 50%, approximately 25% and approximately 0% of the dye and product remaining respectively. A similar indicator 20 and reference template 21 is shown in FIG. 14. The reference template 21 is divided into five sections 22–26 which roughly correspond to the amount of dye and product remaining as the sections 13–17 discussed above. That is, the lack of color in section 22 is indicative of a substantially depleted product. The darkness of section 23 is indicative of an indicator 20 with approximately 25% of the dye and product remaining while the sections 24, 25 and 26 represent the darkness of the indicator 20 with approximately 50%, approximately 75% and approximately 100% of the dye and product remaining respectively.

INDUSTRIAL APPLICABILITY

The present invention comprehends a use-up cue for practical application to any of a number of volatile dispensing products. A method of manufacturing and/or using such a use-up cue is also disclosed.

The foregoing description is given for clearness of understanding only, and no unnecessary limitation should be understood therefrom, as modifications within the scope of the invention may be apparent to those skilled in the art.

We claim:

1. A time duration indicating system for a product, the system comprising:
   a substrate having a volatile air treating component, and
   a volatile dye, wherein the volatile dye is guaiazulene,
   the volatile dye being coated onto the substrate thereby coloring the substrate, the volatile dye evaporating over time resulting in a color change for the substrate.

2. The time duration indicating system of claim 1, wherein the volatile component is N,N-diethyl-m-toluamide.

3. The time duration indicating system of claim 1, wherein the volatile component is transfluthrin.

4. The time duration indicating system of claim 1, wherein the substrate is made from a material selected from the group consisting of cellulose, matted glass fibers, paper, ceramic, felt, woven fabric, nonwoven fabric, and polymeric powders or mixtures thereof.

5. The time duration indicating system of claim 1, further comprising a retarder selected from the group consisting of hexadecane, tetradecene, transfluthrin, dodecene, N,N-diethyl-m-toluamide, vapothin, permethin, prallethrin, tefluthrin, and esbiothrin.

6. The time duration indicating system of claim 1, further comprising a reference template having a color substantially the same as the substrate coated with the volatile dye and prior to any substantial volatilization of said dye.

7. The time duration indicating system of claim 1, further comprising a reference template having a color substantially the same as the substrate after substantially all of the dye has been volatized.

8. The time duration indicating system of claim 1, wherein the volatile component is an insect repellant.

9. The time duration indicating system of claim 1, further comprising a solvent, the volatile dye being dissolved in the solvent to form an intermediate solution, the substrate being coated with the intermediate solution.

10. The time duration indicating system of claim 9, wherein the solvent is selected from the group consisting of isoparaffinic hydrocarbon solvents, heptane, methanol, acetone, ethanol, isopropyl alcohol, dodecene and tetrahydrofuran or mixtures thereof.

11. The time duration indicating system of claim 1, wherein the volatile component is an insecticide.

12. The time duration indicating system of claim 11, wherein the insecticide is a pyrethroid.

13. The time duration indicating system of claim 11, wherein the insecticide is selected from the group consisting of transfluthrin, vapothrin, permethrin, prallethrin, tefluthrin and esbiothrin.

14. A method for indicating an end of life of a product, the method comprising:

provising a substrate having a volatile air treating component;

providing a solvent and a retarder;

mixing a volatile dye with the solvent and the retarder to form an intermediate solution; and coating the substrate with the intermediate solution containing the volatile dye and the retarder thereby coloring the substrate, the volatile dye volatilizing over time resulting in a color change for the substrate and thereby indicating the end of the life of the product.

15. The method of claim 14, wherein the volatile dye is guaiazulene and the volatile component is an insecticide.

16. The method of claim 14, wherein the volatile dye is guaiazulene and the volatile component is transfluthrin.

17. The method of claim 14, wherein the retarder is selected from the group consisting of hexadecane, tetradecene, transfluthrin, dodecene, N,N-diethyl-m-toluamide, vapothrin, permethrin, prallethrin, tefluthrin, and esbiothrin.

18. A method for indicating an end of life of a product, the method comprising:

providing a substrate having a volatile air treating component;

providing a retarder;

mixing a volatile dye with the retarder; and coating the substrate with the volatile dye and the retarder thereby coloring the substrate, the volatile dye volatilizing over time resulting in a color change for the substrate and thereby indicating the end of the life of the product.

19. The method of claim 18, wherein the retarder is selected from the group consisting of hexadecane, tetradecene, transfluthrin, dodecene, N,N-diethyl-m-toluamide, vapothrin, permethrin, prallethrin, tefluthrin, and esbiothrin.

20. An insecticide product with an end of life color change indicator, comprising:

a substrate, a volatile insecticide coated onto the substrate, the volatile insecticide selected from the group consisting of transfluthrin, permethrin, permethrin, prallethrin, tefluthrin and esbiothrin, and quaiazulene coated onto the substrate, wherein the color change indicator includes guaiazulene die coated onto the substrate.

21. The insecticide product of claim 20, further comprising a reference template disposed adjacent to the substrate and having a color substantially the same as the substrate coated with the guaiazulene dye and prior to volatilization of the guaiazulene dye.

22. The insecticide product of claim 20, further comprising a reference template disposed adjacent to the substrate and having a color substantially the same as the substrate after substantially all of the guaiazulene dye has been volatized.

* * * * *